United States Patent
Maack et al.

(10) Patent No.: US 6,920,201 B2
(45) Date of Patent: Jul. 19, 2005

(54) X-RAY DEVICE WITH A STORAGE FOR X-RAY EXPOSURE PARAMETERS

(75) Inventors: Hanns-Ingo Maack, Norderstedt (DE); Ulrich Neitzel, Hamburg (DE); Susanne Guenther-Kohfahl, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 103 days.

(21) Appl. No.: 10/318,739

(22) Filed: Dec. 13, 2002

(65) Prior Publication Data

US 2003/0118154 A1 Jun. 26, 2003

(30) Foreign Application Priority Data

Dec. 15, 2001 (DE) .......................... 101 61 708

(51) Int. Cl.⁷ .............................. H05G 1/46; H05G 1/58; H05G 1/30
(52) U.S. Cl. ........................... 378/116; 378/91; 378/95; 378/108; 378/110; 378/112; 378/115
(58) Field of Search .................. 378/8, 16, 91, 378/95, 97, 98.7, 108–113, 115, 116

(56) References Cited

U.S. PATENT DOCUMENTS

| | | | | |
|---|---|---|---|---|
| 4,158,138 A | * | 6/1979 | Hellstrom | .................. 378/116 |
| 4,160,906 A | * | 7/1979 | Daniels et al. | ................ 378/97 |
| 4,597,094 A | * | 6/1986 | Kleinman | ..................... 378/95 |
| 5,231,651 A | * | 7/1993 | Ozaki et al. | .................... 378/4 |
| 5,588,036 A | | 12/1996 | Fujise et al. | |
| 5,737,386 A | | 4/1998 | Strawder | |
| 5,949,811 A | * | 9/1999 | Baba et al. | .................. 378/108 |
| 6,233,310 B1 | * | 5/2001 | Relihan et al. | ............. 378/108 |
| 6,259,767 B1 | | 7/2001 | Neumann et al. | |
| 6,292,537 B1 | * | 9/2001 | Zimmermann | .............. 378/108 |
| 6,542,579 B1 | * | 4/2003 | Takasawa | ................... 378/165 |

FOREIGN PATENT DOCUMENTS

DE     100 19 242 A1    10/2001

* cited by examiner

Primary Examiner—Allen C. Ho

(57) ABSTRACT

The invention relates to an X-ray device in which a set of exposure parameters is fetched from among a number of such sets stored in a first storage arrangement for APR X-ray exposures. The exposure parameters which result therefrom during the subsequent X-ray exposure and have possibly been modified by the user are stored in a second storage arrangement. The X-ray device includes means for evaluating the second sets of exposure parameters which are associated with the same first set of exposure parameters and for deriving therefrom a new set of exposure parameters which is stored in the first storage arrangement instead of the first set of exposure parameters and forms the basis for APR X-ray exposures from then on.

7 Claims, 2 Drawing Sheets

X-RAY DEVICE WITH A STORAGE FOR X-RAY EXPOSURE PARAMETERS

BACKGROUND

The invention relates to an X-ray device which is provided with a storage arrangement for storing a number of sets of exposure parameters, each time one of which can be fetched for a subsequent X-ray exposure.

The use of a storage arrangement in which a respective set of exposure parameters for an X-ray exposure is stored for various organs has since long been known in field of radiography. According to such a so-called APR (APR= Anatomically Programmed Radiography) exposure technique, first exposure parameters for the X-ray generator are stored, for example, the voltage applied to the X-ray tube, the current through the X-ray tube or the mAs product. The advent of so-called digital image detectors has led to additional exposure parameters which are not intended for adjustment of the X-ray generator, for example, the dimensions of the exposure field to be exposed on the digital image detector or image processing parameters.

The advantage of such an X-ray device (known from U.S. Pat. No. 6,259,767) resides in the fact that for an X-ray exposure of the relevant organ the user merely has to fetch the set of exposure parameters associated with the relevant organ, after which the exposure parameters contained therein are automatically adjusted by means of appropriate adjusting means.

The user can change the exposure parameters fetched if the circumstances during the X-ray exposure deviate from the customary exposure situation. When this set of exposure parameters is fetched the next time, the original exposure parameters are supplied again. When the exposure parameters (generally set by the manufacturer of the X-ray device) basically are not optimal in the opinion of the user, the user has to change the exposure parameters each time when the relevant set of exposure parameters is fetched.

In order to avoid the necessity of such constant changing, the stored sets of exposure parameters can be modified by the service department of the manufacturer or, be it for given exposure parameters only, by the user. Considering the large number of sets of exposure parameters (contemporary X-ray devices can store as many as approximately 1000 different sets of exposure parameters), however, this is a rather cumbersome operation.

SUMMARY

It is an object of the present invention to provide an X-ray device whose operation is simplified even further. This object is achieved by means of an X-ray device which includes a first storage arrangement for storing a number of first sets of exposure parameters, each time one of which can be fetched for a subsequent X-ray exposure, means for changing the exposure parameters fetched, a second storage arrangement in which a number of second sets of exposure parameters can be stored, each one of said second sets of exposure parameters containing the exposure parameters, or values derived therefrom, which are actually active during the subsequent X-ray exposure after the fetching of a first set of exposure parameters, means for evaluating the second sets of exposure parameters associated with the same first set of exposure parameters in order to derive a new set of exposure parameters and means for storing the new set of exposure parameters in the first storage arrangement instead of the first set of exposure parameters.

When a set of exposure parameters stored in the first storage arrangement is fetched, in accordance with the invention the exposure parameters actually active during the subsequent X-ray exposure (or values derived therefrom) are stored in a second storage arrangement. When a set of exposure parameters has been fetched sufficiently often from the first storage arrangement, a number of sets of exposure parameters containing the exposure parameters actually active during the X-ray exposures has been stored in the second storage arrangement.

The evaluation reveals the differences between an exposure parameter of a set fetched from the first storage arrangement and the value of this exposure parameter during the subsequent X-ray exposures, so that a new exposure parameter can be determined which has a value which is actually active during the preceding X-ray exposures. When the exposure parameters of the sets stored in the first storage arrangement are replaced by this new exposure parameter, sets of exposure parameters will be obtained which presumably have to be changed less often for future X-ray exposures. The X-ray device thus "learns" the optimum exposure parameters for its relevant group of users. Because different X-ray institutes or clinics customarily use different adjusting techniques, such new sets of exposure parameters may differ from one institute to another.

It is to be noted that many X-ray devices already store a plurality of technical parameters, including the exposure parameters (for the APR technique as well as for the technique with free adjustment). However, this data can usually be accessed only by the manufacturer and it does not serve directly for the adjustment of the relevant X-ray device.

Generally speaking, it may be assumed that an exposure parameter fetched from the first storage arrangement and possibly modified by the user is actually active during the exposure, for example, the tube voltage. However, this does not hold for all exposure parameters. An exposure parameter used in the case of digital detectors is, for example, the so-called exposure index which corresponds to the sensitivity of the film-foil combinations previously used for X-ray exposures and wherefrom the dose required for an optimum exposure is derived. When such an X-ray exposure is carried out with a given mAs product acting as the exposure parameter, the radiation absorption by the relevant patient will decide whether or not the X-ray exposure is indeed carried out in conformity with the preset exposure index. The exposure index cannot be measured directly, but only a variable which is derived therefrom, that is, the dose on the image receiver, be it only after an X-ray exposure.

In accordance with the invention the exposure parameters are not evaluated after each X-ray exposure so that no new exposure parameters are derived and stored in the first storage arrangement. In accordance with a device implementing principles of the present invention such evaluation takes place only after an activation criterion has been satisfied. This criterion may concern, for example, the number of X-ray images formed after the last activation or (for a single set of exposure parameters) a given number of times this set of exposure parameters has been fetched or also a given period of time elapsed since the last activation. In another version in conformity with aspects of the present invention, however, the user or the service department has the possibility of initiating this operation by activation of the adaptation mode.

Another version of a device in conformity with other aspects of the present invention serves to avoid incidental or too frequent changes of the exposure parameters or to preclude adjustments which do not make sense. Therefore, the exposure parameters derived from the evaluation of the second sets of exposure parameters are stored in the first storage arrangement only after having been checked.

DESCRIPTION OF THE DRAWINGS

The invention will be described in detail hereinafter, by way of example, with reference to a flow chart. In the drawings.

DESCRIPTION

Figure 1:
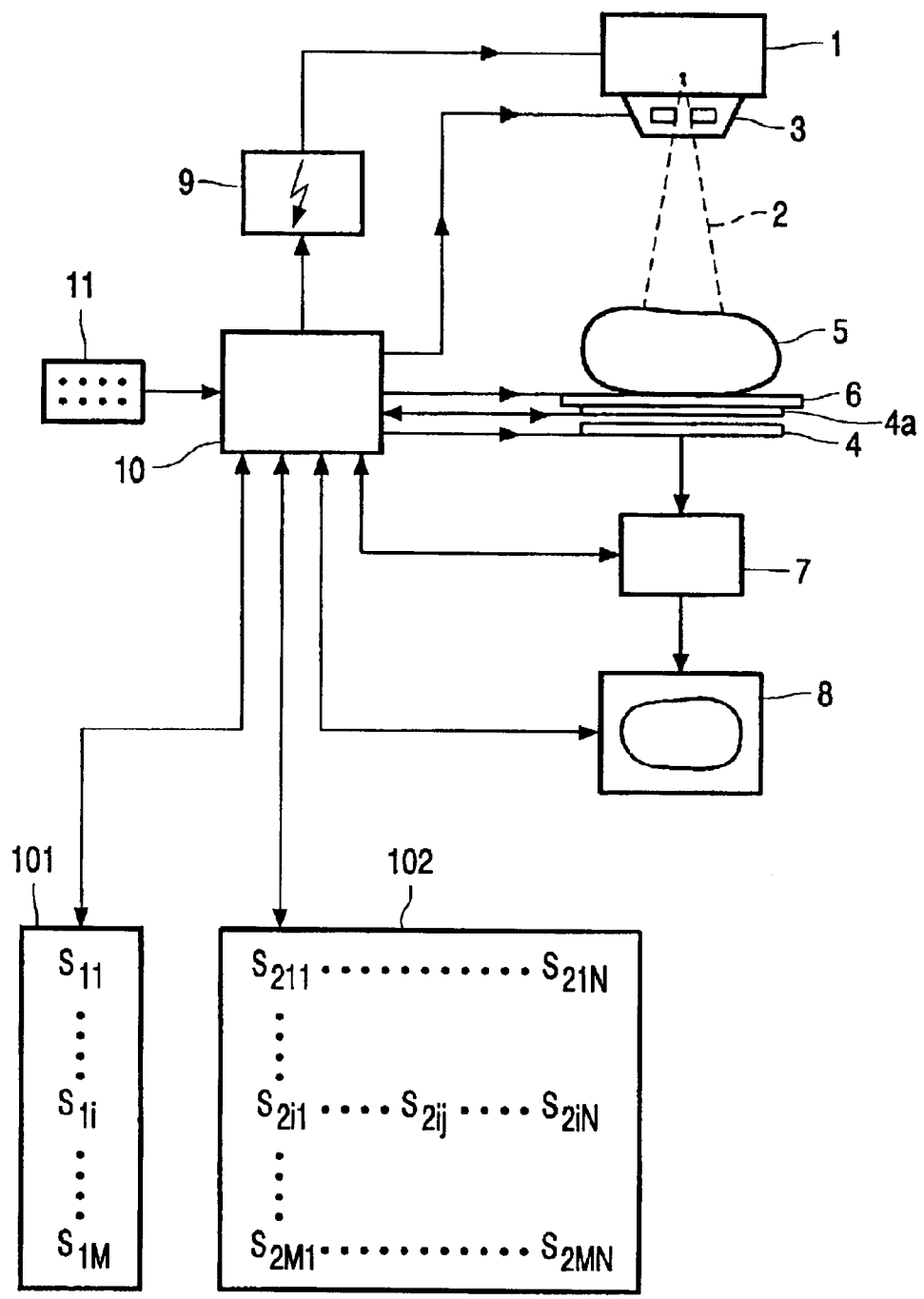
FIG. 1 is a diagrammatic block diagram of an X-ray device.

The X-ray device shown in FIG. 1 includes an X-ray source 1 which emits a radiation beam 2 during an X-ray exposure. The cross-section of this beam can be varied by means of a controllable multi-leaf collimator 3. The radiation beam 2 is incident on an image receiver 4 after having traversed an object 5 to be examined which is situated on the top 6 of an examination table the remainder of which is not shown. Between the image receiver 4 and the table top 6 there is provided a sensor 4a of the automatic exposure device which measures the dose behind the object 5 to be examined.

Even though the invention can also be used in conjunction with an image receiver in the form of a conventional film-foil combination, it will be assumed hereinafter that the image receiver 4 is a so-called digital image detector, that is, a detector which can be electrically read out and delivers image signals which are dependent on the radiation dose at the various points (pixels) of the detector. An X-ray image is reconstructed from these image signals in an image processing unit 7 so as to be displayed on a monitor 8. The X-ray source 1 receives its power supply from an X-ray generator 9.

The components 1 to 9 are controlled by a control unit 10, for example, a workstation, which can be accessed by the operator via an input unit 11. The data input by the user or fetched by the entry made by the user can be displayed on the monitor 8 or on a separate display.

The user can either freely adjust the exposure parameters required for forming an X-ray image or fetch a set of exposure parameters in the case of APR exposures, and the control unit 10 then automatically adjusts the components 1 to 9 accordingly. To this end, the control unit 10 accesses a first storage arrangement 101 in which a number of first sets of exposure parameters $S_{1l} \ldots S_{1i} \ldots S_{1M}$ is stored. Therein, M is the number of first sets of exposure parameters which may amount to more than 1000. Each set of exposure parameters comprises a number L of exposure parameters.

Part of said exposure parameters has been adjusted already before the beginning of an X-ray exposure, for example, the size of the exposure field to be irradiated, or becomes active only during an X-ray exposure, for example, the voltage applied to the X-ray source, or occur only at the end of the exposure, for example, the exposure duration or the dose on the image receiver which can be determined only after the X-ray exposure. Many parameters can be directly adjusted in the form in which they are preset, for example, the voltage applied to the X-ray source (disregarding, of course, adjusting errors). Other parameters, such as the dose on the image receiver 4 or the exposure index which is the inverse thereof, cannot be directly adjusted but are influenced by other exposure parameters such as, for example, the mAs product.

Figure 2:
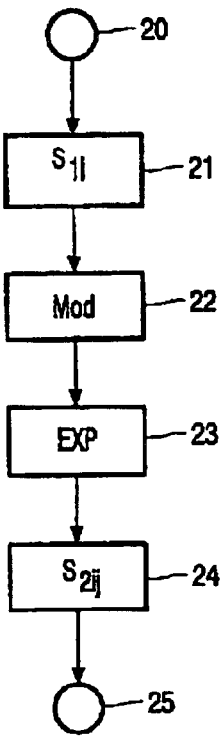
FIG. 2 shows a flow chart of the exposure mode which can be carried out by means of such an X-ray device.

The operation of the X-ray device in the exposure mode in which X-ray images are formed will be described in detail hereinafter with reference to the flow chart of FIG. 2. After the initialization in the step 20, the operator fetches, in step 21, a first set of exposure parameters $S_{1i}$ via the input unit 11, i being between 1 and M. The exposure parameters belonging to this set are displayed to the user, for example, on the monitor 8 and can be modified by the user in the step 22 by means of the input unit 11. In the step 23 an X-ray image is formed while using these preset, possibly modified exposure parameters which have been adjusted via suitable adjusting members in the X-ray device.

In the step 24 the exposure parameters which were active during the exposure are stored. These are exposure parameters which were already contained in the set of parameters fetched, but they may also be modified exposure parameters. Some exposure parameters, for example, the exposure index or the dose on the image receiver, can be determined only after completion of an X-ray exposure (in that integration is performed over the image signals supplied by the image receiver in order to form a mean value).

The exposure parameters active during the X-ray exposure constitute a second set of exposure parameters $S^{2ij}$, the index i of this second set of exposure parameters being linked to the first set of exposure parameters $S_{1i}$ and the index j having a value which is dependent on the number of times the first set of exposure parameters $S_{1i}$ has been fetched. This second set of exposure parameters is stored in a second storage arrangement 102 which is capable of storing N sets of exposure parameters for each first set of exposure parameters, so that the sets of exposure parameters $S_{2i1} \ldots S_{2ij} \ldots S_{2jN}$ are obtained in this memory for the first set of exposure parameters $S_{1i}$. The exposure mode for the relevant X-ray exposure is then terminated (step 25).

Figure 3:
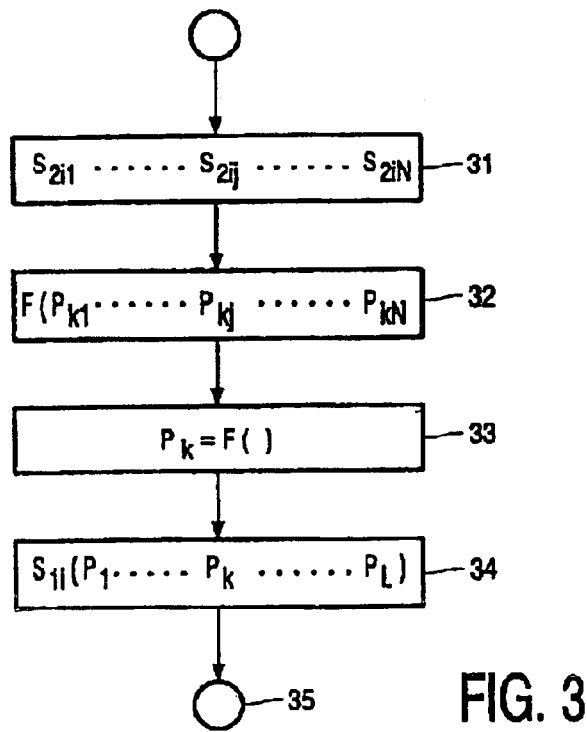
FIG. 3 shows a flow chart of the adaptation mode which can be executed by means of the X-ray device.

Comparison of the sets of exposure parameters stored in the two storage arrangements 101 and 102 takes place either at freely selectable instants or automatically after a predetermined number of X-ray exposures or after a given period of time has elapsed. The X-ray device then operates in an adaptation mode whose flow chart is shown in FIG. 3. To this end, in the step 31 the sets of exposure parameters $S_{2i1} \ldots S_{2iN}$ are fetched which were active during the APR X-ray exposures for which the set of exposure parameters $S_{1i}$ was fetched from the first storage arrangement.

For each exposure parameter $P_k$ of the first set of exposure parameters, for example, the mAs product, the values $P_{k1} \ldots P_{kN}$ active during the N X-ray exposures are analyzed in the step 32 and compared with the parameter $P_k$ contained in the first set of exposure parameters, for example, by forming its arithmetical mean value or median value. The specific evaluation of the exposure parameters may be dependent on the nature of the exposure parameters. Whereas for continuously variable exposure parameters, such as the mAs product or the dimensions of an exposure field, it may be useful to derive an arithmetical mean value or median value from the exposure parameters active during the X-ray exposure, for other exposure parameters (for example, the presence or absence of a scatter grid in the beam path) it may be useful to base the further presets on which of the two possibilities (with scatter grid or without scatter grid) was chosen more frequently during the N exposures.

Before basing the exposure parameters of the set of exposure parameters $S_{1i}$ on the exposure parameter $P_k$ thus determined from the preceding X-ray exposures, it makes sense to perform further tests in the step 33. In order to avoid incidental or too frequent modifications of the exposure parameters, thresholds may be introduced for the adaptation so that an exposure parameter stored thus far in the first storage arrangement is preserved when it has been modified only comparatively rarely. However, if it has been modified comparatively frequently and in the same sense, for example, if the exposure field was enlarged in more than 50 percent of all cases, the relevant exposure parameter is modified accordingly. Furthermore, it may be useful to limit the range of values for the exposure parameters in such a manner that the settings which do not make sense are precluded. Thus, a corresponding value can be assigned to the relevant parameter $P_k$ in the step 33. This is repeated for all exposure parameters $P_1 \ldots P_k \ldots P_L$ of a set, so that a new set $S_{1i}$ of (at least partly modified) exposure parameters is obtained which is stored in the first storage arrangement 101 (step 34) instead of the set used thus far.

The steps 31 . . . 34 can be repeated for other sets of exposure parameters, after which the adaptation mode is terminated (step 35). The adaptation mode, however, can also be automatically activated when an activation criterion is satisfied for an individual set of exposure parameters, for example, when since the last adaptation a given number of X-ray exposures has been carried out while using this fetched set.

As has already been described, for given types of exposure (without automatic exposure device) an mAs product and a given exposure index or a given dose on the image receiver are specified as exposure parameters. These exposure parameters are dependent on one another. In this case in the steps 31 . . . 34 no new value of this exposure parameter is determined from the values of the exposure index or the dose on the image receiver after the exposures, but these values are used to determine a more suitable value of the mAs product. For example, when the evaluation in the step 32 or 33 reveals that on average the receiver dose was a factor of 2 too high during the preceding N exposures (or the exposure index was a factor of 2 too low), the mAs product adjusted for the exposures is reduced by the factor 2 and preset as the new exposure parameter.

Furthermore, there are also exposures which involve an automatic exposure device where the exposure index is subject to a given a sensitivity level of the automatic exposure device for which it is expected that the detector dose typically reaches a given value which is associated with a given sensitivity class (for the specification of the sensitivity classes there are medical standards such as the guidelines for physicians). This sensitivity class can be adapted in the same way as the mAs value. If the evaluation in the step 32 or 33 reveals, for example, that the receiver dose was on average a factor of 2 too high during the preceding N exposures (or the exposure index was a factor of 2 too low), the sensitivity level adjusted for the exposures is lowered by 3 levels (corresponding to a factor of 2) and preset as the new exposure parameter.

It is not necessary to use separate storage arrangements 101 and 102 for storing the first and second sets of exposure parameters. The exposure parameters can be stored in the same memory. The second sets of exposure parameters resulting from the X-ray exposures need not be stored in a given memory location, but can be stored successively; in that case additionally an identification is stored for the fetched first set of exposure parameters.

The invention is of course not limited to the described or shown embodiments, but generally extends to any embodiment, which falls within the scope of the appended claims as seen in light of the foregoing description and drawings. While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

What is claimed is:

1. An X-ray control device comprising:

a means for selecting one of a plurality of x-ray exposure techniques;

a first storage arrangement for storing a number of first sets of preset exposure parameters ($S_{1i} \ldots S_{1i} \ldots S_{1M}$), each first set corresponding to one of the plurality of X-ray exposure techniques;

a manual input means for inputting changes to the preset exposure parameters of the selected first set corresponding to the selected x-ray exposure technique;

a second storage arrangement in which a number of second sets of exposure parameters ($S_{211} \ldots S_{2ij} \ldots S_{2MN}$) are stored, each of said second sets of exposure parameters containing the exposure parameters, or values derived therefrom, which are actually used during performance of the selected X-ray exposure technique;

means for evaluating a plurality of the second sets of exposure parameters ($S_{2i1} \ldots S_{2ij} \ldots S_{2iN}$) corresponding to the same x-ray exposure technique in order to drive a new first set of preset exposure parameters for said same x-ray exposure technique; and means for replacing the previously stored set of preset exposure parameters in the first storage arrangement with the new first set of preset exposure parameters.

2. The X-ray device of claim 1 comprising:

an image receiver which is read out electrically and supplies image signals which are dependent on the radiation dose received in order to form an X-ray image, and means for determining the radiation dose from the image signals after an X-ray exposure, one of the exposure parameters being a dose exposure parameter related to the radiation dose received on the image receiver, and means for calculating a new value of the dose exposure parameter which is necessary so as to realize a preselected radiation dose.

3. The X-ray device of claim 1 comprising:

means for the automatic activation of the evaluating means to evaluate the second sets of exposure parameters and the replacing means to store the new sets of X-ray exposure parameters after an activation criterion has been satisfied.

4. The X-ray device of claim 1 adapted to operate in an exposure mode wherein after each X-ray exposure;

the actively used X-ray exposure parameters are stored in the second storage arrangement, the evaluating means evaluates the actual used exposure parameters, and the replacing means replaces the corresponding exposure parameters in the first storage arrangement with the corresponding new exposure parameters from the evaluating means.

5. The X-ray device of claim 1 comprising:

means for checking the value of an exposure parameter derived from the evaluation of the second sets of exposure parameters ($S_{2i1}$ ... $S_{2ij}$ ... $S_{2iN}$) before it replaces a corresponding exposure parameter in the first storage arrangement.

6. An X-ray apparatus comprising:

an X-ray source which directs X-rays through an examination region and an X-ray detector which receives X-rays which have passed through the examination region;

a controller which controls at least the X-ray source in accordance with designated exposure parameters;

a preset exposure parameter memory in which a set of preset exposure parameters corresponding to each of a plurality of exposure techniques are stored;

an operator console including a display which displays at least a selected set of preset exposure parameters;

an operator input through which the selected set of preset exposure parameters are changeable;

an actually used exposure parameter memory which stores exposure parameters that are actually used in each X-ray exam;

a processor programmed for performing the steps of:

analyzing the actually used exposure parameters stored in the actually used exposure parameter memory corresponding to each of a plurality of the preselected exposure techniques to determine deviations between the preselected exposure parameters and the actually used exposure parameters, based on the determined deviations, determining new exposure parameters for each corresponding exposure technique, and substituting the new exposure parameters for the preset exposure parameters in the preset exposure parameter memory for each of the exposure techniques.

7. A method of controlling an X-ray device which includes a preset exposure parameter memory for storing preset exposure parameters for each of a plurality of X-ray exposure techniques, the method comprising:

(a) selecting one of the preselected exposure techniques and retrieving the corresponding present exposure parameters from the preset exposure parameter memory;

(b) displaying the retrieved exposure parameters and providing for changing one or more of the displayed exposure parameters to select exposure parameters for actual use;

(c) conducting an X-ray exposure using the actually used exposure parameters;

(d) storing the actually used exposure parameters;

(e) repeating steps (a)–(d);

(f) evaluating the actually used exposure parameters for each of a plurality of the exposure techniques to derive new exposure parameters;

(g) substituting the new exposure parameters for the preset exposure parameters stored in the preset exposure parameter memory.

* * * * *